US010835102B2

(12) United States Patent
Ganapati et al.

(10) Patent No.: US 10,835,102 B2
(45) Date of Patent: Nov. 17, 2020

(54) TUNABLE COLOR-TEMPERATURE WHITE LIGHT SOURCE

(71) Applicant: Verily Life Sciences LLC, Mountain View, CA (US)

(72) Inventors: Vidya Ganapati, San Jose, CA (US); Supriyo Sinha, Menlo Park, CA (US); Eden Rephaeli, Menlo Park, CA (US)

(73) Assignee: VERILY LIFE SCIENCES LLC, Mountain View, CA (US)

( * ) Notice: Subject to any disclaimer, the term of this patent is extended or adjusted under 35 U.S.C. 154(b) by 637 days.

(21) Appl. No.: 15/222,471

(22) Filed: Jul. 28, 2016

(65) Prior Publication Data

US 2018/0028047 A1   Feb. 1, 2018

(51) Int. Cl.
| A61B 1/06 | (2006.01) |
| A61B 1/07 | (2006.01) |
| A61B 1/00 | (2006.01) |
| G02B 23/24 | (2006.01) |
| A61B 90/30 | (2016.01) |

(52) U.S. Cl.
CPC ...... *A61B 1/00006* (2013.01); *A61B 1/00039* (2013.01); *A61B 1/063* (2013.01); *A61B 1/0638* (2013.01); *A61B 1/0669* (2013.01); *A61B 1/0684* (2013.01); *A61B 1/07* (2013.01); *G02B 23/2469* (2013.01); *A61B 2090/309* (2016.02)

(58) Field of Classification Search
CPC . A61B 1/00006; A61B 1/00039; A61B 1/063; A61B 1/0638; A61B 1/0669; A61B 1/0684; A61B 1/07; A61B 1/0653; A61B 1/0661; A61B 1/043; G02B 23/2469

USPC .......................... 600/178, 179, 180, 181, 182
See application file for complete search history.

(56) References Cited

U.S. PATENT DOCUMENTS

| 5,154,707 A | * | 10/1992 | Rink | .................. A61B 18/22 606/12 |
| 8,517,929 B2 | | 8/2013 | Kuroda et al. | |

(Continued)

FOREIGN PATENT DOCUMENTS

| EP | 1 610 593 A2 | 12/2005 |
| JP | 200768699 A | 3/2007 |

(Continued)

OTHER PUBLICATIONS

Relative spectral power distribution of CIE, International Commission on Illumination, 2 pages.

(Continued)

*Primary Examiner* — Timothy J Neal
*Assistant Examiner* — William B Chou
(74) *Attorney, Agent, or Firm* — Christensen O'Connor Johnson Kindness PLLC

(57) ABSTRACT

A system for medical diagnosis includes a fiber optic cable and a plurality of light emitters optically coupled to a first end of the fiber optic cable. Each light emitter in the plurality of light emitters emits a distinct bandwidth of light. The system also includes a controller electrically coupled to the plurality of light emitters. The controller includes logic that when executed by the controller causes the controller to perform operations including: receiving instructions including an illumination mode, and adjusting an intensity of the light emitted from each light emitter in the plurality of light emitters to match the illumination mode.

24 Claims, 7 Drawing Sheets

(56) References Cited

U.S. PATENT DOCUMENTS

| | | | |
|---|---|---|---|
| 2003/0133292 A1* | 7/2003 | Mueller | A45D 42/10 362/231 |
| 2005/0099824 A1* | 5/2005 | Dowling | A61B 1/0653 362/572 |
| 2005/0194876 A1* | 9/2005 | Shimada | A61B 1/0638 313/110 |
| 2006/0134001 A1* | 6/2006 | Frangioni | A61K 49/0032 424/9.6 |
| 2006/0173245 A1 | 8/2006 | Todd et al. | |
| 2009/0075391 A1* | 3/2009 | Fulghum, Jr. | A61B 1/00165 436/164 |
| 2010/0010314 A1* | 1/2010 | Krattiger | A61B 1/00096 600/182 |
| 2011/0184243 A1 | 7/2011 | Wright et al. | |
| 2011/0234782 A1 | 9/2011 | Ehrhardt et al. | |
| 2011/0245607 A1* | 10/2011 | Hayashi | A61B 1/015 600/109 |
| 2013/0038711 A1* | 2/2013 | Sato | A61B 1/00048 348/68 |
| 2013/0120678 A1* | 5/2013 | Chao | G02F 1/01 349/34 |
| 2013/0188331 A1 | 7/2013 | Jaffe et al. | |
| 2014/0336479 A1* | 11/2014 | Ando | A61B 5/4041 600/310 |
| 2014/0353696 A1* | 12/2014 | Kinoshita | F21K 9/00 257/89 |
| 2015/0362151 A1 | 12/2015 | Van Bommel et al. | |
| 2016/0213226 A1* | 7/2016 | Yanagidate | A61B 1/00009 |
| 2017/0331014 A1* | 11/2017 | Horie | H05B 33/086 |
| 2018/0199803 A1* | 7/2018 | Kamee | A61B 1/00 |
| 2018/0228355 A1* | 8/2018 | Daidoji | A61B 1/06 |
| 2018/0289246 A1* | 10/2018 | Tabata | A61B 1/04 |
| 2018/0368658 A1* | 12/2018 | Yamamoto | A61B 1/00009 |
| 2019/0021580 A1* | 1/2019 | Mishima | A61B 1/00 |

FOREIGN PATENT DOCUMENTS

| | | |
|---|---|---|
| JP | 2012-191225 A | 10/2012 |
| JP | 2013-535084 A | 9/2013 |
| JP | 2015-11127 A | 1/2015 |
| JP | 2016-96935 A | 5/2016 |
| WO | 01/36864 A2 | 5/2001 |
| WO | WO 2004/100611 A1 | 11/2004 |
| WO | 2010/059197 A2 | 5/2010 |

OTHER PUBLICATIONS

International Search Report and Written Opinion dated Nov. 10, 2017, from the International Searching Authority, for International Application No. PCT/US20171043793, filed Jul. 25, 2017, 33 pages.

Office Action dated Feb. 28, 2020, for Japanese Patent Application No. 2019-502001. (with English translation, 8 pages).

* cited by examiner

TUNABLE COLOR-TEMPERATURE WHITE LIGHT SOURCE

TECHNICAL FIELD

This disclosure relates generally to white light sources, and in particular but not exclusively, relates to endoscopic light sources.

BACKGROUND INFORMATION

Endoscopy allows a physician to view organs and cavities internal to a patient using an insertable instrument. This is a valuable tool for making diagnoses without needing to guess or perform exploratory surgery. The insertable instruments, sometimes referred to as endoscopes or borescopes, have a portion, such as a tube, that is inserted into the patient and positioned to be close to an organ or cavity of interest.

Endoscopes first came into existence in the early 1800's, and were used primarily for illuminating dark portions of the body (since optical imaging was in its infancy). In the late 1950's, the first fiber optic endoscope capable of capturing an image was developed. A bundle of glass fibers was used to coherently transmit image light from the distal end of the endoscope to a camera. However, there were physical limits on the image quality this seminal imaging endoscope was able to capture: namely, the number of fibers limited the resolution of the image, and the fibers were prone to breaking.

Now endoscopes are capable of capturing high-resolution images, as endoscopes use various modern image processing techniques to provide the physician with as natural a view as possible. For example, the views provided by an endoscope may be capable of mimicking a natural feeling field and depth of view to emulate a physician seeing with her own eyes.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Figure 1:
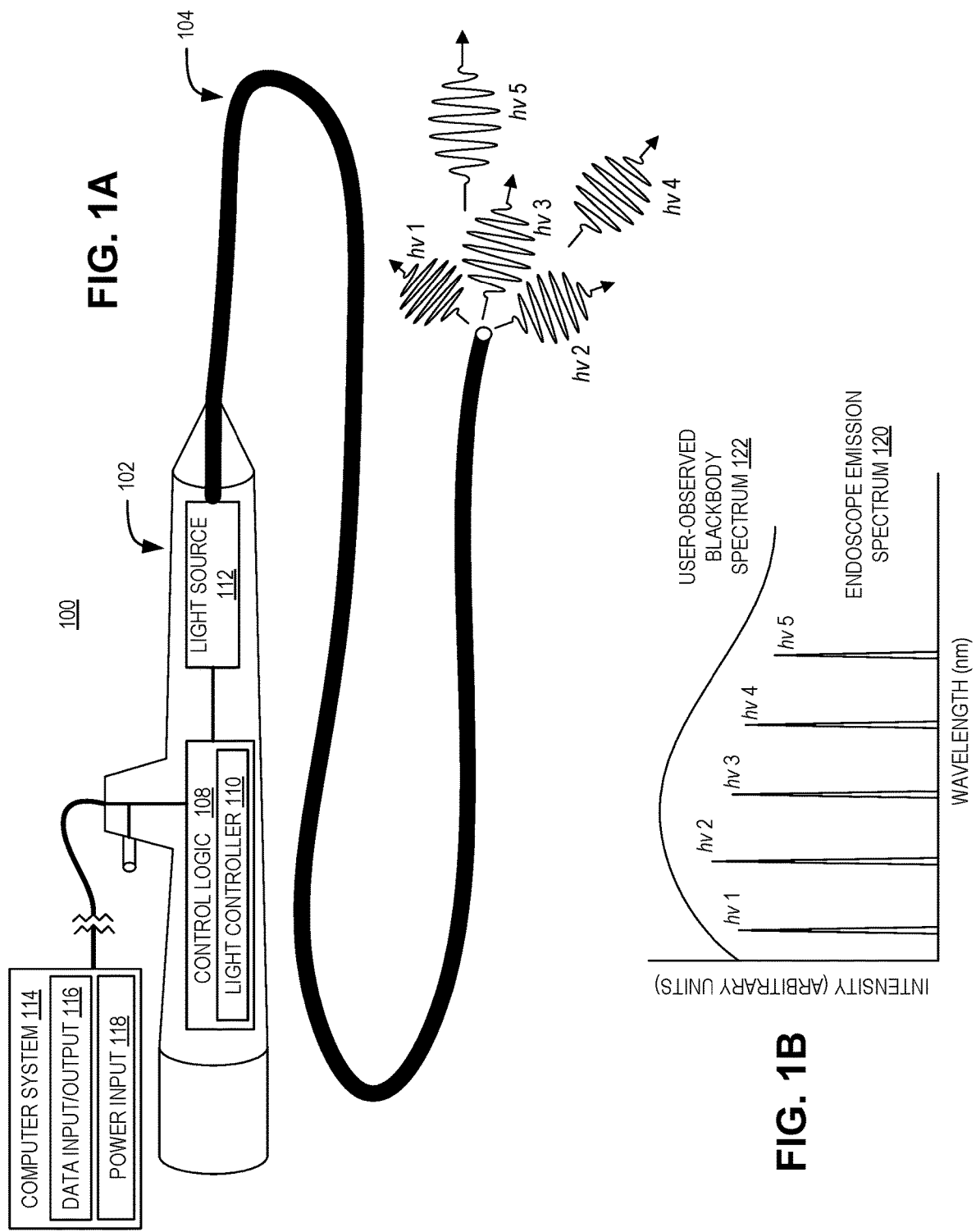
FIG. 1A is a block diagram of an endoscope system, in accordance with an embodiment of the disclosure.
FIG. 1B shows an endoscope emission spectrum and a corresponding blackbody emission spectrum, in accordance with an embodiment of the disclosure.

Embodiments of a system and method for a tunable color-temperature white light source are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Endoscopes are devices physicians use to view inside of patients without the need to perform exploratory surgery. In general, endoscopes are imaging devices with insertion tubes that are inserted into a patient through (small) incisions. The imaging device provides views from a tip ("distal end") of the insertion tube and displays the view, for example, on a monitor for the physician. The imaging system may provide a stereoscopic view of an area of interest so that a more natural image is presented to the viewer. To generate the stereoscopic view, endoscopes may include multiple image sensors, where each image sensor provides an image of the area of interest from a slightly different perspective. The difference in perspective is intended to emulate the different perspective of human eyes. To further enhance endoscope imaging and aid physicians in diagnosis, the instant disclosure provides an elegant solution to produce substantially white light (or another operator-desired emission spectrum) at the distal end of the endoscope.

The color of an object depends on the spectrum of the illumination light source, as well as the object's own spectral reflectance. When imaging with an endoscope inside a cavity, the illumination source is located at the distal end. To make the colors look "natural" and recognizable to the surgeon, a white light source with a spectrum similar to daylight (e.g., a blackbody emission spectrum at 6500° K) is frequently preferred. However, to get the light to the tip of the endoscope, the light source needs to be well-coupled to a fiber optic cable so that the cable can efficiently carry the light to the tip. A broadband lamp or LED can be used as the light source, but coupling efficiency to the fiber may, in some situations, be limited. A laser can couple efficiently to a fiber optic cable; however, the monochromatic laser source will likely produce colors that look unnatural. This may impede the ability of the endoscope operator (e.g., surgeon) from making an accurate diagnosis or properly identify tissue. Additionally, in both the case of laser or broadband illumination, the source emission spectrum is fixed; what looks like "natural" coloring is subjective, so a tunable source is desirable.

As will be discussed in greater detail, a set of discrete lasers are coupled into an illumination fiber bundle, with the relative power of the lasers set by software. The user can set a temperature (T) in the software, and the relative power of the lasers is tuned by the software to illuminate the patient. Thus, the patient looks as if he/she was illuminated by blackbody radiation from an object with the temperature "T". Additionally, in some embodiments, the user can input any source spectrum characteristics, and the software will tune the lasers to match the desired spectrum.

FIG. 1A is a block diagram of endoscope system 100, in accordance with an embodiment of the disclosure. Endoscope system 100 includes: endoscope body 102; fiber optic cable 104; control logic 108; light controller 110; light source 112; and computer system 114 (including data input/output 116, and power input 118). In endoscope system 100, light source 112 includes a plurality of light emitters and is optically coupled to a first end of fiber optic cable 104. Each light emitter in light source 112 emits a distinct bandwidth of light—depicted as the five photons with five different energies exiting the distal (second) end of fiber optic cable 104. Control logic 108 is electrically coupled to the plurality of light emitters to control an emission intensity of each light emitter in the plurality of light emitters. As will be discussed in FIG. 1B, the light output from a second end of fiber optic cable 104 mimics a blackbody emission spectrum to the human eye.

In the depicted embodiment, control logic 108 is coupled to receive user input (from computer system 114) and, in response to the user input, independently change the emission intensity of each light emitter in the plurality of light emitters. However, in a different embodiment, user instructions may be directly input into the endoscope (not an attached computer system 114). Although the illustrated embodiment shows endoscope body 102 hardwired to computer system 114, in other embodiments endoscope body 102 may have its own onboard computer system 114 and interface.

Although not depicted to avoid obscuring certain aspects, endoscope system 100 may have a lens system for transmitting images from an objective lens to the endoscope user (this may include a relay lens system or a bundle of fiber optics). Endoscope system 100 may also have one or more mechanical actuators to guide insertion of fiber optic cable 104, and maneuver fiber optic cable 104 through the body. Control logic 108 (e.g., a microcontroller) is disposed in the system and electrically coupled to the plurality of light emitters. The controller includes logic that when executed by the controller causes the controller to perform a myriad of operations. For example, in addition to controlling light output, control logic 108 may be able to control any of the aforementioned pieces of device architecture (e.g., lens system, image sensors, mechanical actuators, etc.). Control logic 108 may be able to precisely control the distances between lenses to focus an image captured by the endoscope, or manipulate the body of fiber optic cable 104 with the one or more mechanical actuators.

FIG. 1B shows an example endoscope emission spectrum 120 and a corresponding user-observed blackbody emission spectrum 122, in accordance with an embodiment of the disclosure. In the depicted embodiment, endoscope emission spectrum 120 and user-observed blackbody emission spectrum 122 have been superimposed on the same graph; this is for comparison purposes only. Both spectra are not drawn to scale.

As illustrated, endoscope emission spectrum 120 includes five discrete emission peaks. To achieve the five peaks, five lasers are directed into a fiber. By tuning the relative power of the lasers, a scene with color that approximates user-observed blackbody emission spectrum 122 can be rendered. The depicted embodiment may contain, for example, five lasers, with center wavelengths of 415 nm, 462 nm, 520 nm, 575 nm, and 635 nm. All lasers may have a bandwidth of 1 nm. These five laser emission peaks may resemble user-observed blackbody emission spectrum 122 (which is similar to a 6,500° K blackbody emission spectrum).

Figure 2:
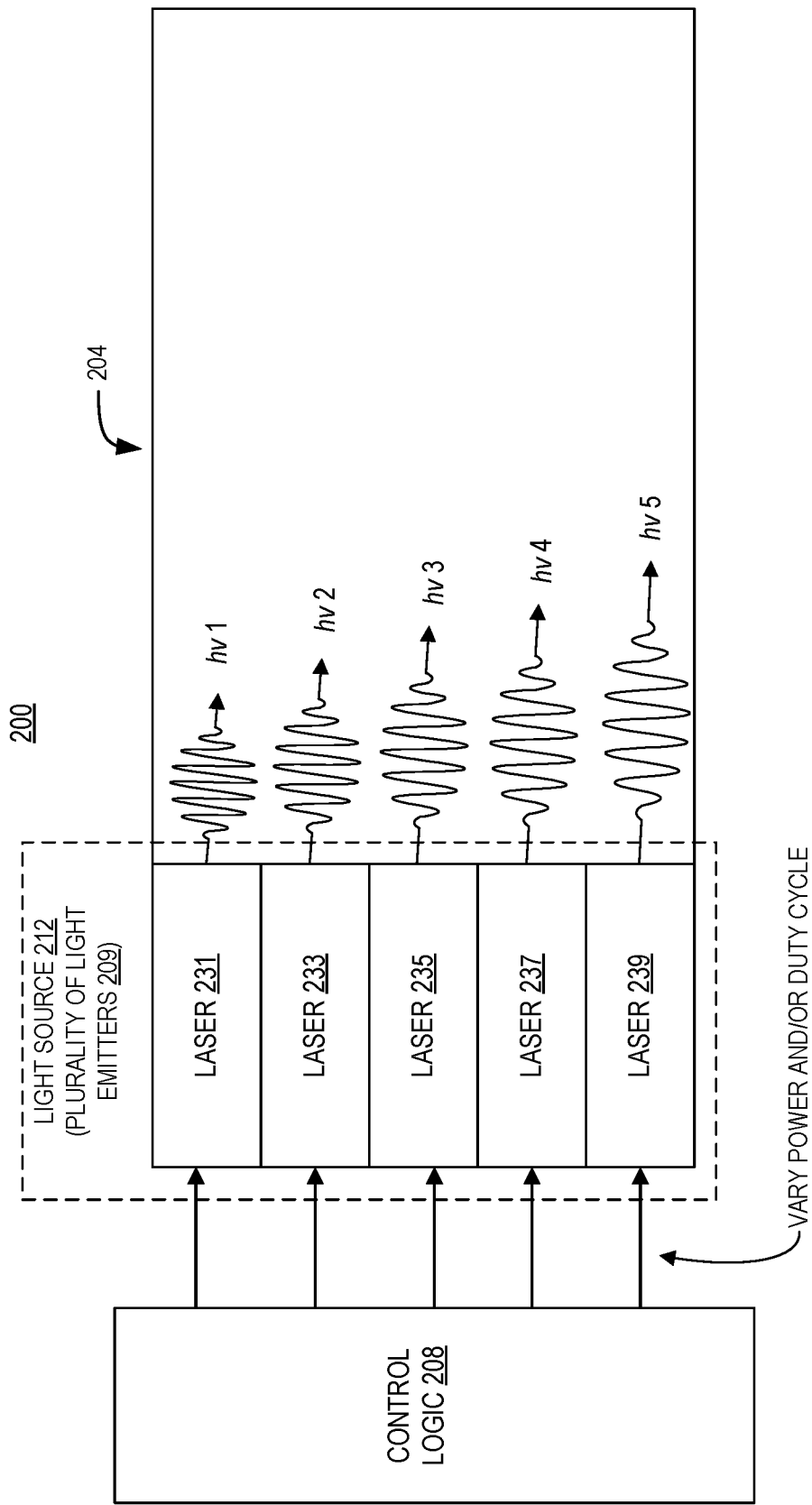
FIG. 2 illustrates an endoscopic light emitter, in accordance with an embodiment of the disclosure.

FIG. 2 illustrates an endoscopic light emitter 200, in accordance with an embodiment of the disclosure. As shown, endoscopic light emitter 200 includes: fiber optic cable 204, light source 212 (including the plurality of light emitters 209), and control logic 208. Plurality of light emitters 209 includes five lasers: laser 231, laser 233, laser 235, laser 237, and laser 239. Each of the plurality of light emitters 209 is optically coupled to fiber optic cable 204, and individually electrically coupled to control logic 208. Plurality of light emitters 209 each emit a discrete wavelength of light. Laser 231 emits the shortest wavelength of light, laser 233 emits the second shortest wavelength of light, laser 235 emits a longer wavelength of light than laser 233, laser 237 emits the second longest wavelength of light, and laser 239 emits the longest wavelength of light. The emission intensity or duty cycle (ratio of on-time to off-time) may be varied to output different emission spectra. For example, the relative intensity (or on time) of laser 231 may be greater when emulating higher temperature (blue-shifted) blackbody emission spectra. Conversely, the relative intensity (or on time) of laser 239 may be greater when emulating lower temperature (red-shifted) blackbody emission spectra.

Although the embodiment depicted in FIG. 2 shows five lasers, in other embodiments plurality of light emitters 209 may have any number of light sources including lasers and/or light emitting diodes. Further, the lasers depicted in FIG. 2 emit relatively monochromatic light (e.g., light with a bandwidth of less than 1 nm). However, in other embodiments, the bandwidth of plurality of light emitters 209 may be larger (on the order of 5 nm or more). In some embodiments, fiber optic cable 204 may include cladding to promote total internal reflection (e.g., the cladding may include a reflective metal, or a material with a lower index of refraction than the bulk of fiber optic cable 204) or contain multiple fibers. An image sensor may be coupled to the distal end of the fiber optic cable 204, or an image sensor may be contained in the body of the endoscope, and the fiber optic cable 204 may be used to relay image light back to the image sensor.

FIGS. 3A-3I illustrate black body emission spectra (left) and corresponding endoscopic emission spectra (right) ranging from 1,500 to 10,000° K, in accordance with several embodiments of the disclosure. Each spectrum depicted is merely one example of many possible emission spectra. All of the endoscopic emission spectra depicted here include five separate light sources (e.g., laser diodes, light emitting diodes, gas lasers, etc.). In all of these embodiments, a user may input a temperature of blackbody emission, and the endoscope will output an endoscopic emission spectrum that resembles the blackbody emission spectrum (to the human eye). In other words, the endoscope's discrete emission peaks can be tuned to trick the human eye into seeing a blackbody emission spectrum or other continuous spectrum, such as a phosphor spectrum.

Figure 3A:
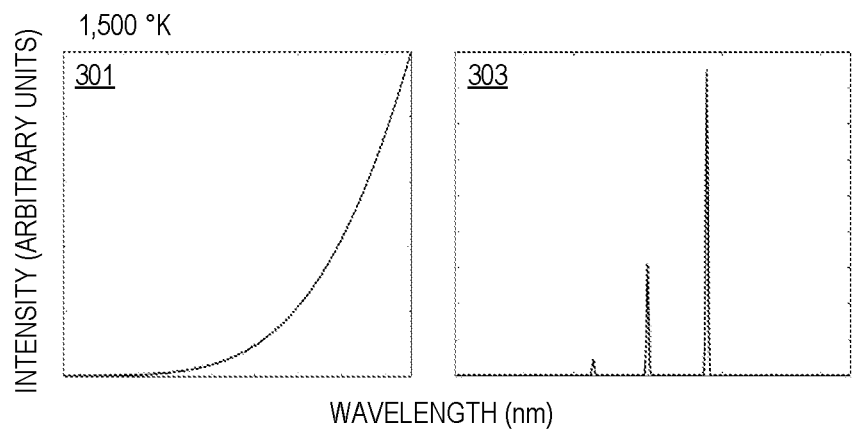
FIGS. 3A-3I illustrate black body emission spectra and corresponding endoscopic emission spectra, in accordance with several embodiments of the disclosure.

FIG. 3A shows a 1,500° K blackbody emission spectrum 301, and the corresponding endoscopic emission spectrum 303. The relatively low-temperature blackbody spectrum is red-shifted. Accordingly, only three low-energy endoscopic emission peaks are used to approximate blackbody emission spectrum 301. The intensity of these peaks increase monotonically in order of decreasing wavelength.

Figure 3B:
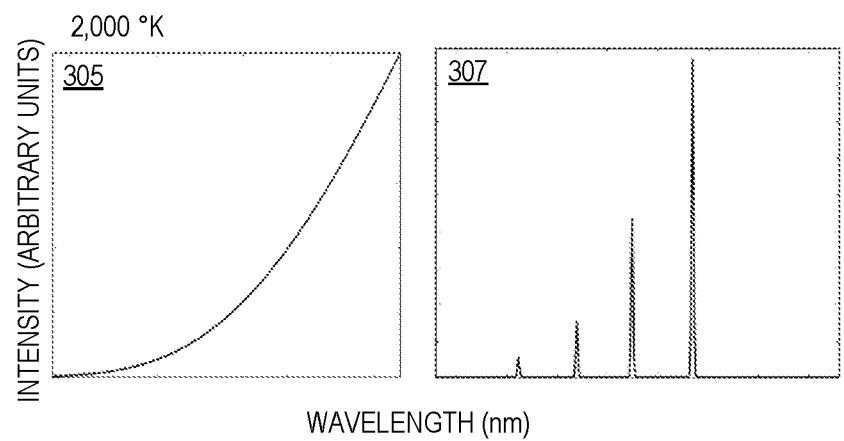

FIG. 3B shows a 2,000° K blackbody emission spectrum 305, and the corresponding endoscopic emission spectrum 307. Similarly to FIG. 3A, the relatively low-temperature blackbody spectrum is red-shifted. Thus, only four low-energy endoscopic emission peaks are used to approximate blackbody emission spectrum 307. The intensity of these peaks increase monotonically in order of decreasing wavelength.

Figure 3C:
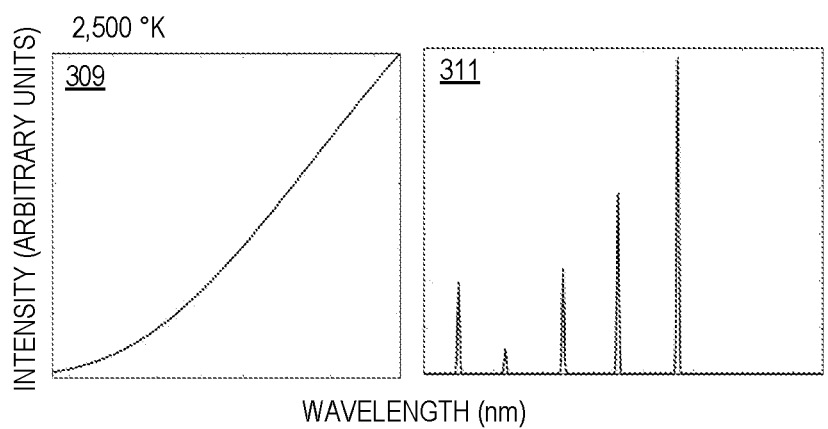

FIG. 3C shows a 2,500° K blackbody emission spectrum 309, and the corresponding endoscopic emission spectrum 311. At 2,500° K blackbody emission spectrum 309 starts to blue-shift but is still red-dominant. Accordingly, the lowest energy peak still has the largest intensity, the second lowest energy peak has the second largest intensity, and the middle peak has a lower intensity than the second lowest energy peak. The second highest energy peak has the lowest intensity, and the highest energy peak has the fourth largest intensity.

Figure 3D:
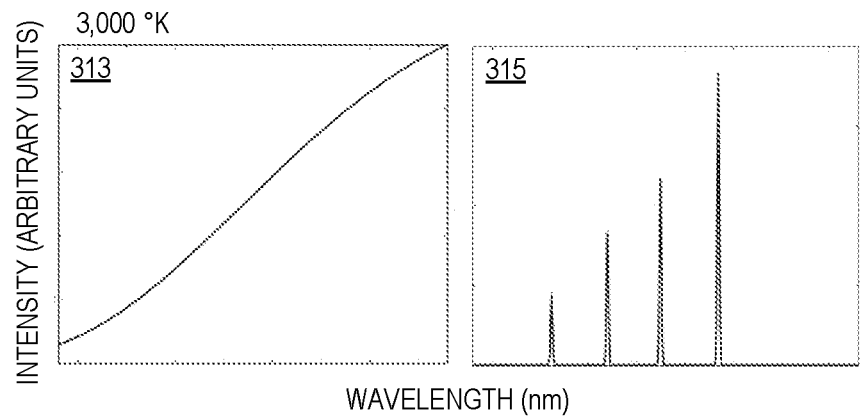

FIG. 3D shows a 3,000° K blackbody emission spectrum 313, and the corresponding endoscopic emission spectrum 315. Here, despite the blackbody emission spectrum 313 blue-shifting relative to the 2,500° K spectrum, only four of the five lasers are used to form the corresponding endoscopic emission spectrum 315. As shown, the four lowest energy lasers are used to emit the spectrum, and the intensity of each emission peak increases monotonically in order of decreasing wavelength.

Figure 3E:
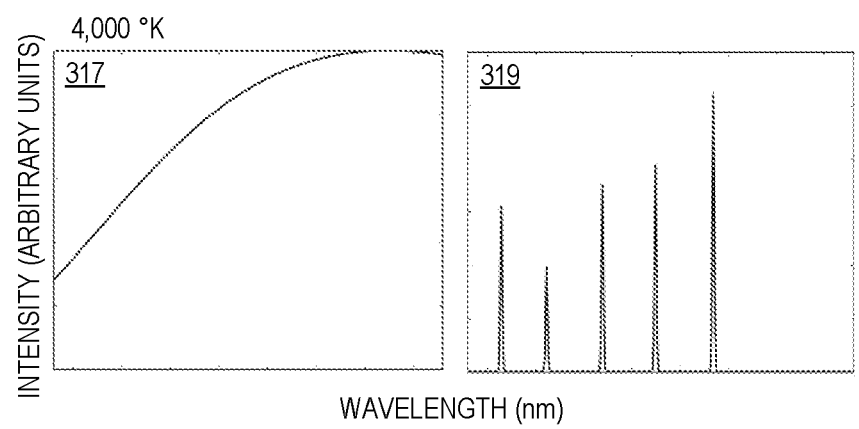

FIG. 3E shows a 4,000° K blackbody emission spectrum 317, and the corresponding endoscopic emission spectrum 319. Blackbody emission spectrum 317 continues to blue-shift, but is still red dominant. Accordingly, endoscopic emission spectrum 319 includes all five laser emission peaks. The highest energy peak has the second lowest intensity, the second highest energy peak has the lowest intensity, the middle energy peak has the third largest intensity, the second lowest energy peak has the second largest intensity, and the lowest energy peak has the largest intensity.

Figure 3F:
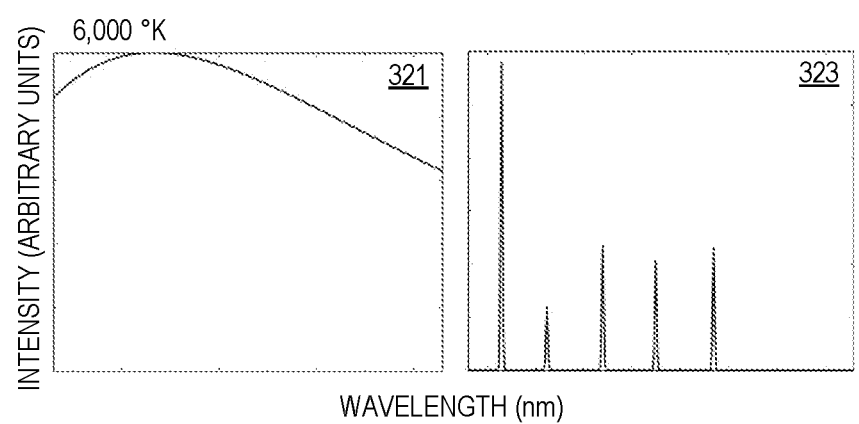

FIG. 3F shows a 6,000° K blackbody emission spectrum 321, and the corresponding endoscopic emission spectrum 323. At 6000° K, blackbody emission spectrum 321 shows a dramatic blue-shift. To match this shift, the highest energy (lowest wavelength) endoscopic emission peak intensity is at least two times larger than the other peaks. However, the second highest energy peak intensity has a lower intensity than all other peaks. The three lowest energy peak intensities are roughly the same size, but the middle peak (second to lowest energy) is slightly smaller than the other two peaks.

Figure 3G:
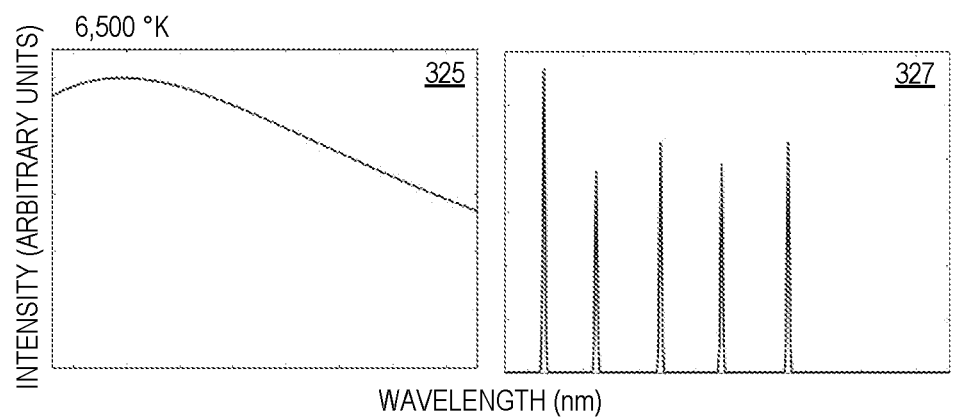

FIG. 3G shows a 6,500° K blackbody emission spectrum 325, and the corresponding endoscopic emission spectrum 327. At 6,500° K blackbody emission spectrum 325 resembles the solar spectrum. It is prominently blue-shifted. The highest energy peak intensity is the largest, the second highest energy peak has the smallest peak intensity, the middle energy peak intensity is larger than the second highest energy peak intensity, and the second lowest energy peak has roughly the same peak intensity as the second highest energy peak intensity. Lastly, the lowest energy peak has roughly the same peak intensity as the middle energy peak.

Figure 3H:
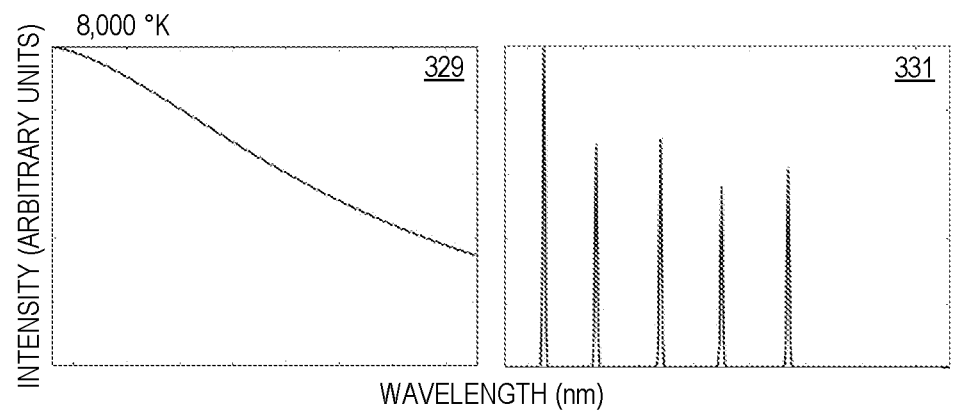

FIG. 3H shows an 8,000° K blackbody emission spectrum 329, and the corresponding endoscopic emission spectrum 331. At 8,000° K, the blackbody emission spectrum 329 is greatly blue-shifted. Endoscopic emission spectrum 331 is also blue-shifted, with the highest energy peak having the greatest intensity, the second highest energy peak having a lower intensity then the highest energy peak, the third highest energy peak having roughly the same intensity as the second highest energy peak, the second lowest energy peak having the lowest intensity, and the lowest energy peak having the second lowest intensity.

Figure 3I:
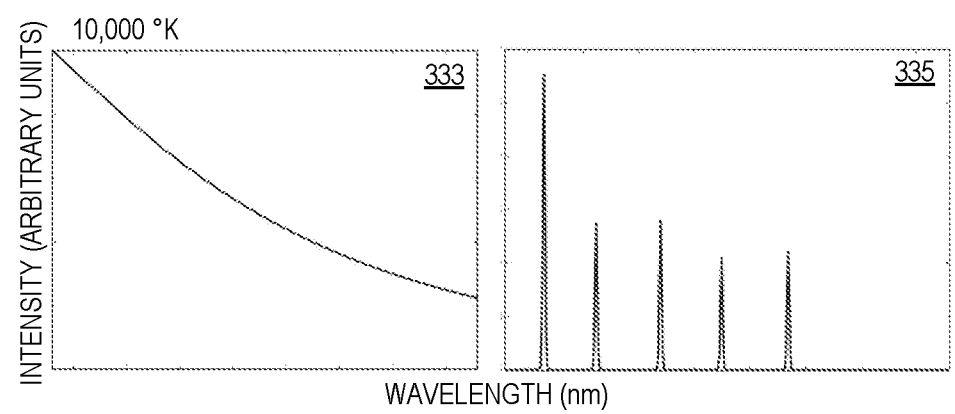

FIG. 3I shows a 10,000° K blackbody emission spectrum 333, and the corresponding endoscopic emission spectrum 335. Blackbody emission spectrum 333 is the most blue-shifted spectrum depicted. Thus, endoscopic emission spectrum 335 is also highly blue-shifted. The highest energy peak is approximately twice as large as every other peak. The next two highest energy peaks are approximately half the size of the highest energy peak, and the two lowest energy peaks are approximately the same size and have a lower intensity than the previous two peaks.

One skilled in the art will observe several trends associated with the above blackbody emission spectra, and their corresponding endoscopic emission spectra: (1) when the temperature of the blackbody emission spectrum is less than 2,500° K the plurality of light emitters emit a monotonically increasing spectrum of light (where the light emitter in the plurality of light emitters with the shortest wavelength emission spectrum has the smallest amplitude, and the light emitter in the plurality of light emitters with the longest wavelength emission spectrum has a largest amplitude); (2) when the temperature of the blackbody emission spectrum is less than 4,000° K, the light emitter in the plurality of light emitters with the longest wavelength emission spectrum has the largest amplitude; and (3) when the temperature of the blackbody emission spectrum is greater than 4,000° K, the light emitter in the plurality of light emitters with the shortest wavelength emission spectrum has the largest amplitude.

Figure 4:
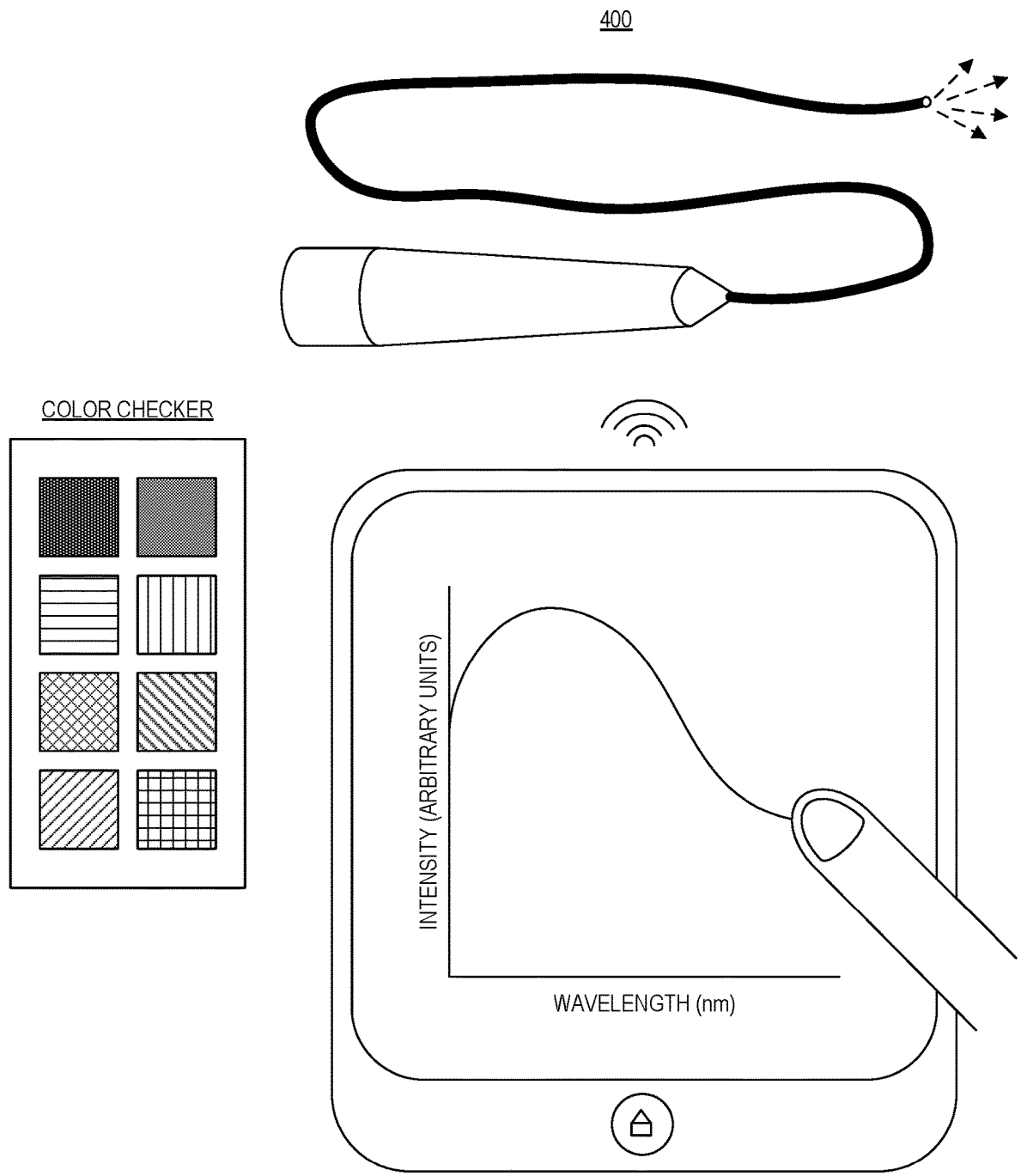
FIG. 4 illustrates a user creating an endoscope emission spectrum, in accordance with an embodiment of the disclosure.

FIG. 4 illustrates a user creating an endoscope emission spectrum, in accordance with an embodiment of the disclosure. As shown, the light emission mode is selected by the user via inputting parameters of a custom continuous emission spectrum into a tablet (or other electronic device). In the depicted embodiment, the user draws the emission spectrum on the screen of a tablet with his/her finger. The tablet wirelessly communicates to endoscope 400, and endoscope 400 adjusts its emission spectra to match the spectra drawn on the tablet. One skilled in the art will appreciate that while the illustrated embodiment involves a person drawing the desired spectra on a tablet, any number of other methods for defining a continuous emission spectra may be used. For example, emission parameters may simply be entered into a table, or the relative peak intensity may be increased/decreased with toggles. Alternatively, a picture may be taken of a scene under a certain kind of illumination, and the tablet may analyze the spectra and adjust the output of endoscope 400 accordingly. Further, any computer system (not just a tablet) may be used to communicate with endoscope 400 either wirelessly, by wire, or other electronic communication method.

Also shown in FIG. 4 is a color checker (a series of squares with idealized colors) which, in some embodiments, may be a "Macbeth" color checker. The color checker includes colors that are meant to represent a range of colors seen in photographs. In one embodiment, selecting a light emission mode may include determining the colors in a color checker under a desired illumination, and generating endoscopic spectral output to match the desired illumination mode. The color checker can be imaged under a reference illuminant (such as a blackbody at 6500° K), and then imaged again under a custom light source. The colors under the custom light source can be compared with the colors under the reference source to see how close the output of the custom source is to the reference. By doing this, endoscope 400 can simulate the desired custom illumination mode. In one embodiment, imaging the color checker may be accomplished with a camera in the tablet (or any other camera device such as a cell phone camera, computer camera, or the like). Alternatively, rather than using a color checker to set the desired spectral output, the endoscope operator could also set the emitted spectrum to enhance the color of a particular organ. This may make diagnosis and treatment easier. For example, a tumor may look different from healthy tissue under different types of light; the endoscope user could adjust the spectra to emit predominantly this diagnostic wavelength of light.

To perform the calculations discussed above, and determine the color of an object (or square in the color checker) the tablet or other computer must calculate the color of an object in XYZ space. The illuminance spectrum ("$I(\lambda)$") first has to be multiplied by the color-specific reflectivity spectrum ("$R(\lambda)$, $G(\lambda)$, $B(\lambda)$") of the object. This spectrum is multiplied by the appropriate curve ($\overline{x}(\lambda)$ for the X value of the color, $\overline{y}(\lambda)$ for the Y value of the color, and $\overline{z}(\lambda)$ for the Z value of the color), and then integrated (see equations 1, 2, and 3).

$$X = \int I(\lambda) R(\lambda) \overline{x}(\lambda) d\lambda \quad \text{Equation 1:}$$

$$Y = \int I(\lambda) G(\lambda) \overline{y}(\lambda) d\lambda \quad \text{Equation 2:}$$

$$Z = \int I(\lambda) B(\lambda) \overline{z}(\lambda) d\lambda \quad \text{Equation 3:}$$

In the representation of color, there are two primary concepts: "colorfulness" (i.e., the amount of color) and "luminosity" (i.e., the brightness of the color). It takes two terms to represent the colorfulness and one term to represent the luminosity. "Colorfulness" may be determined by calculating u' and v' using X, Y, and Z (see equations 4 and 5).

$$u' = 4X/(X+15Y+3Z) \quad \text{Equation 4:}$$

$$v' = 9Y/(X+15Y+3Z) \quad \text{Equation 5:}$$

When comparing the color to a reference illuminant, we can calculate $\Delta(u'v')$ (see equation 6).

$$\Delta(u'v') = \sqrt{((u'-u'_{ref})^2 + (v'-v'_{ref})^2)} \quad \text{Equation 6:}$$

Ideally $\Delta(u'v') \leq 0.030$. In this range, the human eye has difficulty perceiving the difference between the colors. In other words, the optimization seeks to minimize the sum (or some other linear combination) of the difference between the color of a tile (or other color reference) under broadband normal illumination (e.g., blackbody illumination at 6500° K) and the color of that same tile under illumination from the set of lasers described here.

Figure 5:
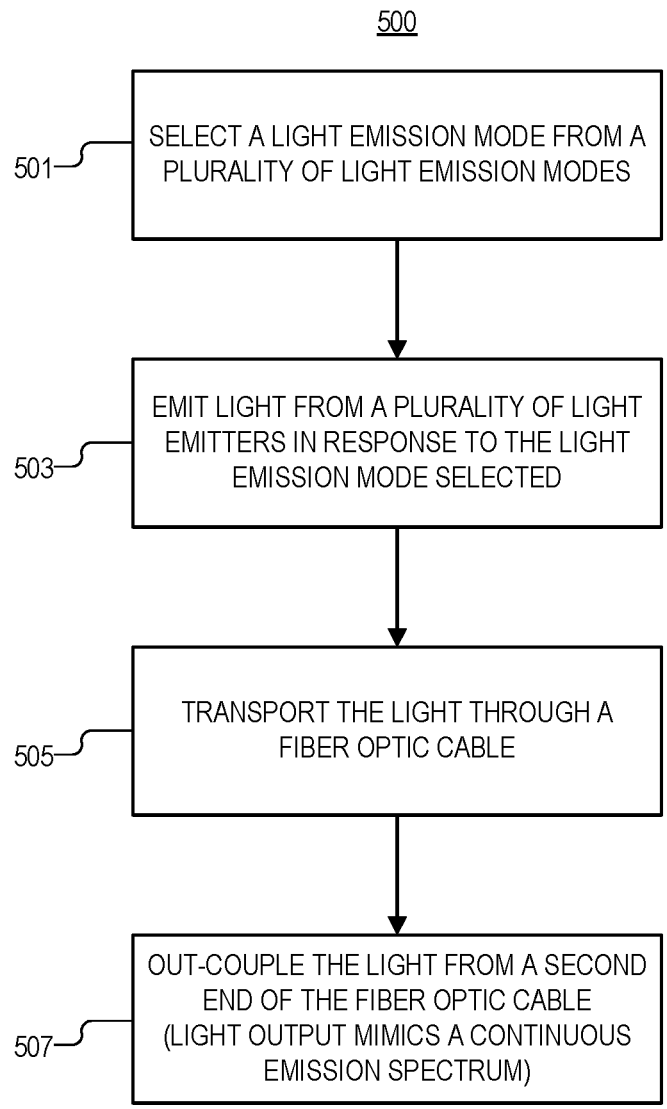
FIG. 5 illustrates method of endoscopic illumination, in accordance with an embodiment of the disclosure.

FIG. 5 illustrates method 500 of endoscopic illumination, in accordance with an embodiment of the disclosure. The order in which some or all of process blocks 501-507 appear in method 500 should not be deemed limiting. Rather, one of ordinary skill in the art having the benefit of the present disclosure will understand that some of method 500 may be executed in a variety of orders not illustrated, or even in parallel.

Block 501 shows selecting a light emission mode from a plurality of light emission modes. In one embodiment, the light emission mode is any one of the endoscopic emission spectrums corresponding to a blackbody emission spectrum depicted in FIGS. 3A-3I. In other embodiments, the user may select, trace, or input a custom emission spectrum (see e.g., FIG. 4).

Block 503 illustrates emitting light from a plurality of light emitters in response to the light emission mode selected. In one embodiment, each light emitter in the plurality of light emitters emits a distinct bandwidth of the light. The bandwidth of light emitted by most light emitters in the plurality of light emitters may be less than 5 nm. In other embodiments, the bandwidth may be appreciably smaller, such as 1 nm or less.

Block 505 depicts transporting the light through a fiber optic cable; a first end of the fiber optic cable is optically coupled to the plurality of light emitters. In some embodiments, using lasers as the light source provides for extremely efficient light coupling to the fiber optic cable (relative to other white light sources).

Block 507 shows out-coupling the light from a second end of the fiber optic cable, and the light output from the second end of the fiber optic cable mimics a continuous emission spectrum to the human eye. In one embodiment, the light output from the second end of the fiber optic cable mimics a blackbody emission spectrum by having a $\Delta(u'v') \leq 0.030$ from the blackbody emission spectrum, in a CIELUV color space.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A system for medical diagnosis, comprising:
a fiber optic cable;
a plurality of light emitters optically coupled to a first end of the fiber optic cable, wherein each light emitter in the plurality of light emitters emits a distinct bandwidth of light; and
a controller disposed in the system and electrically coupled to the plurality of light emitters, wherein the controller includes logic that when executed by the controller causes the controller to perform operations including:
generating reference image data based on a scene under reference illumination from a reference illuminant;
receiving instructions including an illumination mode, wherein the illumination mode is based on the reference image data;
adjusting an intensity of the light emitted from each light emitter in the plurality of light emitters to match the illumination mode;
generating illumination mode image data based on the scene illuminated under the illumination mode; and
comparing the reference image data and the illumination mode image data.

2. The system of claim 1, wherein the illumination mode includes a set of predefined intensities of the light for the plurality of light emitters to emit.

3. The system of claim 2, wherein the set of predefined intensities mimic a blackbody emission spectrum corresponding to a temperature, and wherein the temperature includes a specific temperature between 1,000° K and 10,000° K, inclusive.

4. The system of claim 3, wherein when the temperature of the blackbody emission spectrum is less than 4,000° K a light emitter in the plurality of light emitters with a longest wavelength emission spectrum has a largest intensity, and wherein when the temperature of the blackbody emission spectrum is greater than 4,000° K a light emitter in the plurality of light emitters with a shortest wavelength emission spectrum has a largest intensity.

5. The system of claim 2, wherein the illumination mode mimics the blackbody emission spectrum by having a $\Delta(u'v') \leq 0.030$ from the blackbody emission spectrum, in a CIELUV color space.

6. The system of claim 1, wherein a bandwidth of the light emitted by most light emitters in the plurality of light emitters is less than 5 nm.

7. The system of claim 1, wherein generating reference image data includes taking a picture with a camera, and wherein the illumination mode is based on an analysis of the picture.

8. A method of endoscopic illumination, comprising:
generating reference image data based on a scene under reference illumination from a reference illuminant;
selecting a light emission mode from a plurality of light emission modes based on the reference image data;
emitting light from a plurality of light emitters in response to the light emission mode selected, wherein each light emitter in the plurality of light emitters emits a distinct bandwidth of the light;
transporting the light through a fiber optic cable, wherein a first end of the fiber optic cable is optically coupled to the plurality of light emitters;
out-coupling the light from a second end of the fiber optic cable, wherein the light output from the second end of the fiber optic cable mimics a continuous emission spectrum of the reference illumination to a human eye;
generating light emission mode image data based on the scene illuminated under the light emission mode; and
comparing the reference image data and the light emission mode image data.

9. The method of claim 8, wherein each light emission mode in the plurality of light emission modes corresponds to a temperature of a blackbody emission spectrum between 1,000° K and 10,000° K, inclusive.

10. The method of claim 9, wherein when the temperature of the blackbody emission spectrum is less than 2,500° K the plurality of light emitters emit an emission spectrum that increases monotonically with increasing wavelength, wherein a light emitter in the plurality of light emitters with a shortest wavelength emission spectrum has a smallest intensity, and a light emitter in the plurality of light emitters with a longest wavelength emission spectrum has a largest intensity.

11. The method of claim 9, wherein when the temperature of the blackbody emission spectrum is less than 4,000° K a light emitter in the plurality of light emitters with a longest wavelength emission spectrum has a largest intensity.

12. The method of claim 9, wherein when the temperature of the blackbody emission spectrum is greater than 4,000° K a light emitter in the plurality of light emitters with a shortest wavelength emission spectrum has a largest intensity.

13. The method of claim 9, wherein light output from the second end of the fiber optic cable mimics the blackbody emission spectrum by having a $\Delta(u'v') \leq 0.030$ from the blackbody emission spectrum, in a CIELUV color space.

14. The method of claim 9, wherein the plurality of light emitters includes five laser diodes with a bandwidth of 5 nm or less.

15. The method of claim 9, wherein the light emission mode is selected by a user by inputting parameters of a custom continuous emission spectrum.

16. The method of claim 9, wherein selecting a light emission mode includes:
determining a color of a color checker under the reference illumination; and
generating an illumination mode to match the reference illumination.

17. An endoscope, comprising:
a fiber optic cable;
a reference illuminant;
a camera;
a plurality of light emitters optically coupled to a first end of the fiber optic cable, wherein each light emitter in the plurality of light emitters emits a distinct bandwidth of light; and
control logic electrically coupled to the plurality of light emitters to control an emission intensity of each light emitter in the plurality of light emitters, wherein the light output from a second end of the fiber optic cable is based on reference image data of a scene illuminated by the reference illuminant and generated by the camera, wherein the control logic includes logic that when executed by the controller causes the endoscope to perform operations including:
generating illumination mode image data based on the scene illuminated under the illumination mode; and
comparing the reference image data and the illumination mode image data.

18. The endoscope of claim 17, wherein the control logic is coupled to receive user input and, in response to the user input, independently change the emission intensity of each light emitter in the plurality of light emitters.

19. The endoscope of claim 18, wherein the user input includes a temperature of a blackbody emission spectrum.

20. The endoscope of claim 19, wherein the temperature ranges from 1,000° K to 10,000° K.

21. The endoscope of claim 19, wherein the light output from the second end of the fiber optic cable mimics the blackbody emission spectrum by having a $\Delta(u'v') \leq 0.030$ from the blackbody emission spectrum, in a CIELUV color space.

22. The endoscope of claim 17, wherein the plurality of light emitters includes at least one of a plurality of laser diodes or a plurality of light emitting diodes.

23. The endoscope of claim 22, wherein a bandwidth of light emitted by most light emitters in the plurality of light emitters is less than 5 nm.

24. The endoscope of claim 23, wherein the plurality of light emitters includes five light emitters.

* * * * *